(12) United States Patent
Kugelmeier et al.

(10) Patent No.: US 8,911,690 B2
(45) Date of Patent: Dec. 16, 2014

(54) DEVICES FOR THE PRODUCTION OF CELL CLUSTERS OF DEFINED CELL NUMBERS AND CLUSTER SIZES

(75) Inventors: Patrick Kugelmeier, Zollikerberg (CH); Roger Lehmann, Zürich (CH); Wolfgang Moritz, Basserdorf (CH); Richard Zuellig, Zürich (CH)

(73) Assignee: Universitat Zurich, Zurich (CH)

( * ) Notice: Subject to any disclaimer, the term of this patent is extended or adjusted under 35 U.S.C. 154(b) by 0 days.

(21) Appl. No.: 13/315,944

(22) Filed: Dec. 9, 2011

(65) Prior Publication Data

US 2012/0149051 A1 Jun. 14, 2012

Related U.S. Application Data

(63) Continuation of application No. PCT/EP2010/058136, filed on Jun. 10, 2010.

(30) Foreign Application Priority Data

Jun. 10, 2009 (EP) .................................. 09007703

(51) Int. Cl.
| | |
|---|---|
| B01L 3/00 | (2006.01) |
| G01N 31/16 | (2006.01) |
| C12Q 1/02 | (2006.01) |
| C12M 1/22 | (2006.01) |
| C12M 3/00 | (2006.01) |
| C12N 5/00 | (2006.01) |
| C12N 5/02 | (2006.01) |
| C12M 1/32 | (2006.01) |
| C12M 1/12 | (2006.01) |
| C12M 1/00 | (2006.01) |

(52) U.S. Cl.
CPC ............... *C12M 25/04* (2013.01); *C12M 23/12* (2013.01)
USPC ....... 422/553; 435/29; 435/289.1; 435/305.2; 435/325

(58) Field of Classification Search
CPC ................................................ B01L 2300/0858
USPC .............................. 435/29, 289.1, 305.2, 325
See application file for complete search history.

(56) References Cited

U.S. PATENT DOCUMENTS

| | | | |
|---|---|---|---|
| 5,449,620 | A | 9/1995 | Khillan |
| 6,027,695 | A * | 2/2000 | Oldenburg et al. ............. 506/39 |
| 2004/0101948 | A1* | 5/2004 | Muser ........................ 435/287.1 |
| 2005/0118711 | A1 | 6/2005 | Nordheim et al. |
| 2006/0141612 | A1* | 6/2006 | Yamamoto et al. ........ 435/287.2 |
| 2008/0193421 | A1 | 8/2008 | Kruse et al. |
| 2010/0068793 | A1 | 3/2010 | Ungrin et al. |
| 2011/0086375 | A1 | 4/2011 | Ungrin et al. |

FOREIGN PATENT DOCUMENTS

| | | |
|---|---|---|
| WO | WO 01/02539 A1 | 1/2001 |
| WO | WO 2004/078352 A2 | 9/2004 |
| WO | WO 2008106771 A1 * | 9/2008 |

OTHER PUBLICATIONS

International Search Report dated May 25, 2011 of international application PCT/EP 2010/058136 on which this application is based.
Lehmann et al, "Superiority of Small Islets in Human Islet Transplantation", Diabetes, vol. 56, Mar. 2007, pp. 594 to 603.
Cavallari, G. et al, "Rat Pancreatic Islet Size Standardization by the 'Hanging Drop' Technique", Transplantation Proceedings, 2007, pp. 2018-2020, 39, Elsevier Inc., New York, New York.
Khademhosseini, A. et al, "Co-culture of human embryonic stem cells with murine embryonic fibroblasts on microwell-patterned substrates", Biomaterials, 2006, pp. 5968 to 5977, 27, Elsevier Ltd.
Mohr, J. et al, "3-D microwell culture of human embryonic stem cells", Biomaterials, 2006, pp. 6032-6042, 27, Elsevier Ltd.

* cited by examiner

*Primary Examiner* — Jill Warden
*Assistant Examiner* — Julie Tavares
(74) *Attorney, Agent, or Firm* — Walter Ottesen P.A.

(57) ABSTRACT

Devices for the in vitro aggregation of cells. The devices are characterized by containing special ground cavities allowing cluster formation to take place when a cell suspension is seeded onto the device. Further, the present invention relates to a method for aggregating cells and the use of the devices of the present invention for the aggregation of cells.

14 Claims, 11 Drawing Sheets

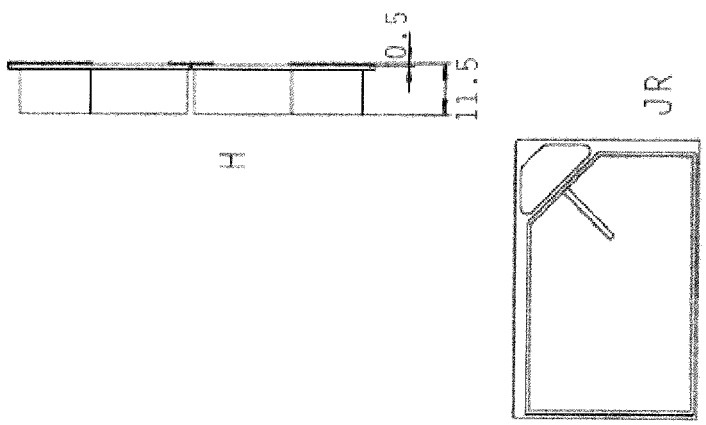
FIG. 3B-B
FIG. 3H
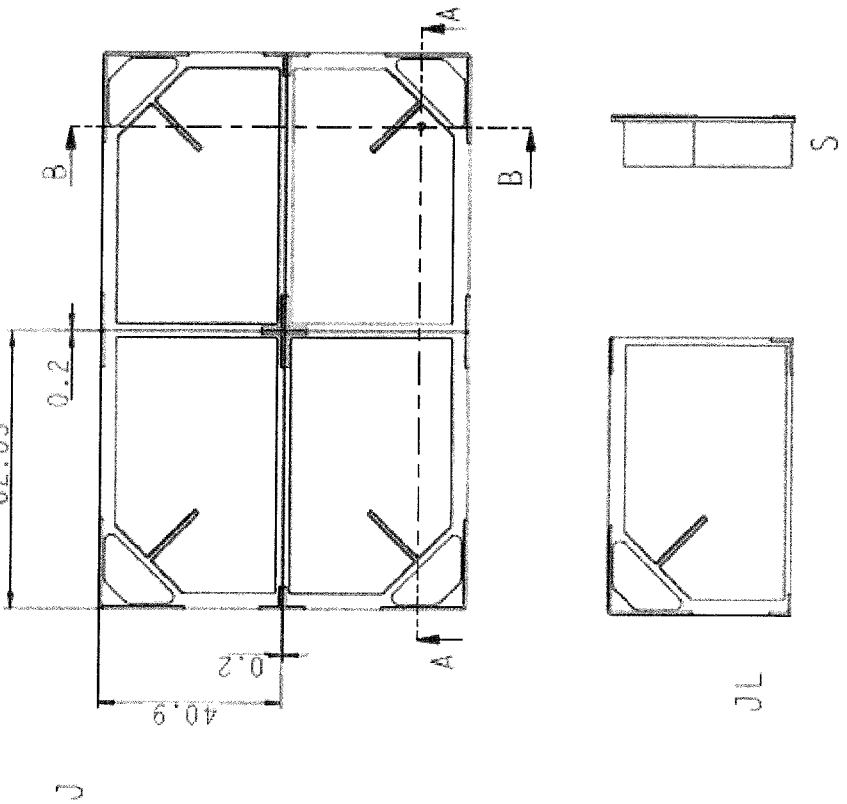
FIG. 3J
FIG. 3JL
FIG. 3JR
FIG. 3S

FIG. 4A-A

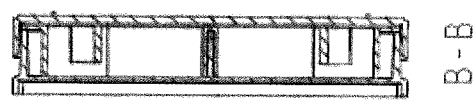
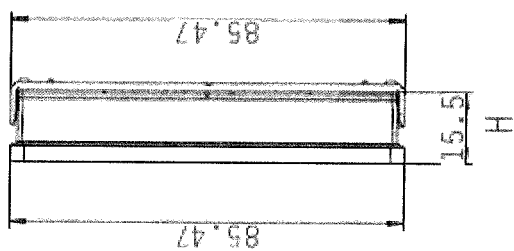
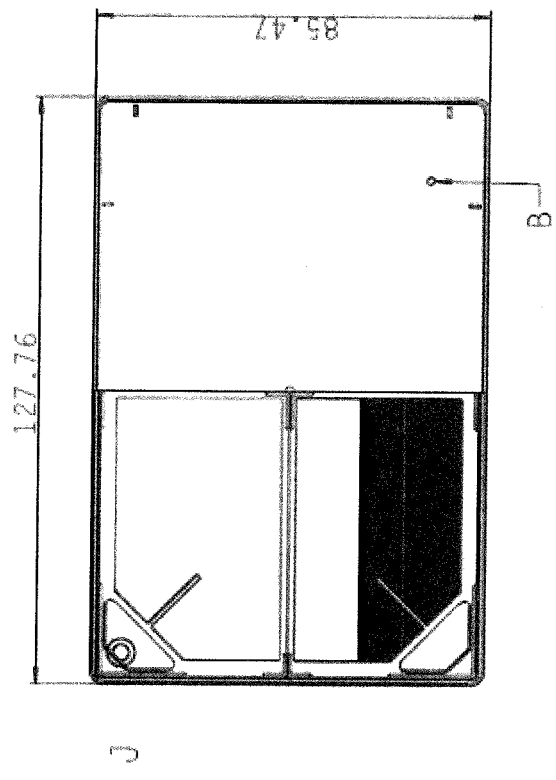
FIG. 4B-B
FIG. 4H
FIG. 4J

DEVICES FOR THE PRODUCTION OF CELL CLUSTERS OF DEFINED CELL NUMBERS AND CLUSTER SIZES

CROSS REFERENCE TO RELATED APPLICATIONS

This application is a continuation application of international patent application PCT/EP 2010/058136, filed Jun. 10, 2010, designating the United States and claiming priority from European application 09007703.3, filed Jun. 10, 2009, and the entire content of both applications is incorporated herein by reference.

FIELD OF THE INVENTION

The present invention relates to devices for the in vitro aggregation of cells. The devices are characterized by containing special ground cavities allowing cluster formation to take place when a cell suspension is seeded onto the device. Further, the present invention relates to a method for aggregating cells and the use of the devices of the present invention for the aggregation of cells.

The present invention allows for the large scale production of defined cell clusters with minimal cell loss and the possibility of performing medium changes, which is not possible with the classic hanging drop cell culture.

BACKGROUND OF THE INVENTION

Stem cell research is studying the principles of tissue regeneration processes in order to develop methods for regenerative medicine. One very important factor of stem cell biology is the constant communication between the stem cells themselves and the interplay of the stem cells and the surrounding tissue, the so called stem cell "niche". Together, these cells form organizational units, cell clusters or "microorgans" that in large number and sophisticated architecture ultimately form an entire organ.

These processes are being studied in various experimental settings of which one of the most classical ones is the use of "hanging drops," where stem cell development can be simulated by putting a certain amount of stem (and other) cells together in a drop in a way that cell clusters develop which can be analyzed. One major disadvantage of this widely used technology is the limited number of cell clusters that can be generated and the impossibility of performing a medium change, which would be most desirable because stem cell differentiation is dependent on the sequential change in cytokine signaling which could be triggered by providing these cytokines with a medium change.

In clinical settings, the prospect of large scale production of cell clusters of defined size with the possibility of performing a medium change would be very desirable for various therapeutic approaches, such as islet cell transplantation. In this technique, small islets perform better than large ones because of the limited diffusion based nutrient and oxygen supply in the early post transplant period (Lehmann R. et al, Diabetes. 2007 March; 56(3): 594 603). It therefore would be desirable to make the large islets small. However, for successful production of small islets and clinical applications, islets would need to be dissociated into single cells and reaggregated to small "pseudoislets." About 1,000,000 pseudoislets would be needed for transplantation, a number impossible to reach with hanging drop technology.

In United States patent application publications 2011/0086375 and 2010/0068793 a device for the production of cell aggregates is described. The device sold as Aggrewell (Stemcell Technologies, Vancouver, BC, Canada V5Z 1B3) is, however, of limited use for stem cell cluster production as well as for islet cell transplantation, because in stem cell cluster production the design of the ground cavities plays a major role due to the possibility of exogenally induced morphogen release and subsequent uncontrolled differentiation. In the device sold as Aggrewell, the cells are being pushed into pyramidal alignment due to the pyramidal cavity design with sharp tips, which can lead to the aforementioned morphogen release. Additionally, in this device the borders between the cavities have a width that allows single cells to rest on the borders, a state which needs to be avoided, again due to the possibility of uncontrolled cytokine release. Furthermore, this device does not have any defined medium change construction, which for stem cell applications would be very desirable as the sequential, rigorously defined application of various cytokines applied by medium changes is crucial for correct stem cell differentiation.

In islet transplantation, this device cannot be used because of the limited number of ground cavities per plate well; a plate with several thousand ground cavities per well would be needed in the art in order to make clinical applications possible. Additionally, in islet transplantation, the formation of clusters needs to be well supported by defined cavities because the microarchitecture of reaggregated pseudoislets in hanging drops resembles original islet architecture with similar spatial distribution of alpha, delta and beta cells which apparently have biological reasons (Cavallari, Moritz et al., ADA 2007 presentation number 2062 P). In the Aggrewell ground cavities, again, the sharp bottoms would push the cells into a non natural form with unknown biological and clinical consequences.

Besides Aggrewell, other groups also performed experiments on micron scale cavities and the cultivation of stem cells and generation of cell clusters (Khademhosseini 2006, Mohr 2006), but due to vertical sidewalls, widely spaced cavities and broad borders the cell cluster formation is not taking place in a controlled manner and results in substantial non uniformities. Future possible stem cell applications target the regeneration and/or replacement of damaged tissue. It is of utmost importance to assure that the differentiation of stem cells is rigorously controlled in order to avoid uncontrolled differentiation and hence tumor formation. Therefore, uncontrolled cytokine and/or morphogen release due to experimental conditions like the ones in the aforementioned devices need to be strictly avoided.

There is therefore a need in the art to provide a device that allows for the aggregation of cells, especially of stem and islet cells and preferably allows for the generation of uniform cell clusters with minimal differentiation or cell cluster formation disturbance by the cavity design. Additionally, the number of cavities should be high in order to produce substantial numbers of cell aggregates. Furthermore, the borders between the cavities should be as small as possible in order to avoid uncontrolled resting of single cells besides the clusters. Moreover, the device should be designed in a way that a controlled medium change is possible. All of these requirements are fulfilled by the present invention.

SUMMARY OF THE INVENTION

An object of the present invention is to provide devices for the aggregation of cells and preferably for the in vitro production of cell clusters of defined cell numbers and sizes for use in research, tissue regeneration or replacement and cell transplantation.

These objects are achieved by providing the devices according to the present invention as defined in the claims.

BRIEF DESCRIPTION OF THE DRAWINGS

The invention will now be described with reference to the drawings wherein:

FIG. 1D shows two adjacent cavities from a side view, "h" indicates cavity height, "α" indicates the possible wall angles;

FIG. 1E shows the bottom of the cavities of the most preferred embodiment with "R" indicating the ground of the spherical bottom;

FIG. 1C shows a top view of the most preferred embodiment with "c" indicating the edge length of the quadrangular top opening of the cavities. In the most preferred embodiment, cavity height h is 350 µm, wall angle α is 54.7 degrees, the spherical bottom R has a diameter of 80 µm to 100 µm and top opening edges length c being is 546 µm with these edges being less than 15 µm broad in order to avoid resting of cells on these edges;

FIGS. 2A-A, 2B-B, 2C, 2D, 2E, 2G, 2H, 2J and 2P show an overview of the most preferred embodiment comprised of a standard SBS footprint cell culture plate (the same size of classical 6, 12, 24 or 96-well plates, 127.76 mm long, 85.47 mm broad and 14-15.5 mm high, depending on whether filling inserts are in place or not) with four defined compartments of whom the ground is covered with the defined ground cavities. Numbers are given in millimeters. In these FIGS., the filling inserts are in place and there is no lid on the cell culture plate;

FIG. 2A-A shows a cross section through the cell culture plate through the plane of cut A;

FIG. 2B-B shows a cross section through the cell culture plate through the plane of cut B;

FIG. 2 G shows the broad side seen from outside; and,

FIG. 2H shows the narrow side seen from outside.

FIG. 2P shows a perspective view of the cell culture plate;

FIGS. 2D, 2E and 2C are equal to FIGS. 1D, 1E and 1C;

FIGS. 3A-A, 3B-B, 3G, 3H, 3J and 3P show the filling inserts alone in the same views as in FIGS. 2A-A, 2B-B, 2G, 2H, 2J and 2P, respectively. Additionally, the four inserts are shown separately;

FIG. 3PL shows a perspective view from the insert in the left upper corner;

FIG. 3JL shows a top view from the insert in the left upper corner;

FIG. 3S shows a side view from the inserts in the left upper corner and FIG. 3JR shows a top view of the insert of the right upper corner. The size of the inserts is shown in FIG. 3J with numbers given in millimeters; one insert is 62.05 mm long, 40.9 mm broad and 11.5 mm high with additional 0.5 mm small bridges for controlled gas exchange, either realized here (shown) and on the plate (not shown) or on the lid itself (not shown);

FIGS. 4A-A, 4B-B, 4G, 4H, 4J and 4P show the same as FIGS. 2A-A, 2B-B, 2G, 2H, 2J and 2P, respectively, but with half of the lid of the cell culture plate added on the right side; and, FIGS. 5A-A, 5B-B, 5G, 5H, 5J and 5P show the same as FIGS. 2A-A, 2B-B, 2G, 2H, 2J and 2P, respectively but without the filling inserts in place. This is the situation after the seeding of the cells and before the first medium change. In the outer edges of the four compartments, the "filling surface" can be seen, where the pipet tip is meant to be placed in order to perform a controlled medium change.

DESCRIPTION OF THE PREFERRED EMBODIMENTS OF THE INVENTION

Figure 1E:
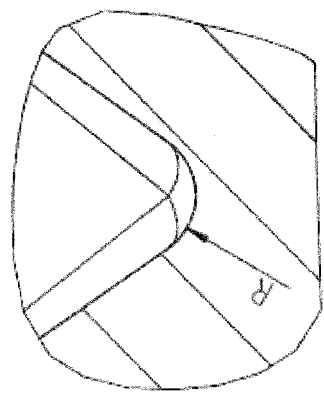
FIGS. 1C, 1D and 1E show a close up model of the ground cavities of the most preferred embodiment. Shaded surfaces indicate solid material.

The device is preferably a cell culture plate with defined ground cavities allowing defined cell numbers to descend to the ground (by gravity or centrifugation) and get close to each other, making aggregation possible. The design of the cavities maximizes initial cell sliding, maximizes cavity number per surface, promotes physiological cluster formation and supports later cluster harvesting by the following specifications.

The kind of suspension for initial cell seeding needs to be individually determined according to the individual experimental or clinical needs. The number of cells and the volume of the suspension can be calculated according to the number of ground cavities of the possible embodiments of the present invention and the intended cell number of the individual clusters. The possible number of cells per ground cavity can range from 0 (i.e. seeding less than 1 cell per cavity so that every 2nd cavity has got 1 cell and clonal growth of 1 individual starting cell can be studied) to several thousand cells per cavity. The exact number of cells required per cavity depends on the individual needs and varies with the type of cells used. In order to reach cluster sizes between 80 and 100 µm diameter which is considered to be the preferred cluster size for reaggregated islet cell transplantation, a number of 100 up to 400 beta cells is needed, depending on cell size, which varies between species and depends on experimental design. With very small cells in other experimental settings, 1,000 cells or more may be needed to reach a diameter of 100 µm; if bigger clusters are required, the number of cells can rise to 8,000 cells for a diameter of 200 µm or 27,000 cells for a diameter of 300 µm (volume~diameter$^3$) and so on.

Medium composition, medium height, metabolic activity and cluster size determine oxygen tension in the cavity environment and subsequently the oxygen gradient in the formed clusters. The oxygen tension plays crucial roles in cell metabolism, differentiation and cell fate determination of stem cells and survival of metabolically active cells, i.e. islet cells. The defined cluster sizes reached by the present invention allow for excellent control of oxygen tension. The relation of cluster size, core oxygenation and cell death of transplanted islets due to low oxygenation in the early posttransplant period has been extensively studied (Lehmann R. et al, Diabetes. 2007 March; 56(3): 594 603); in the present invention, this key problem of islet cell transplantation has been overcome by generating "pseudoislets" of defined (small) cluster sizes with good core oxygenation due to short oxygen diffusion distances, as mentioned above. The cell clusters can be used to regenerate or replace tissue or bone in mammals, preferably humans.

The accessibility of the reaggregating islets allows optionally for additional treatment with regeneration factors such as, but not limited to, cytokines or hormones to enhance islet mass and survival.

The basic form of the cavities consists of a conical or pyramidal shape. Preferably the cavity is a cone with a rounded tip or a cone with a frustrum. It is further preferred that the cavity is a pyramid with a rounded tip or a pyramid with a frustrum.

The form of the bottoms of the cavities can take on various shapes. In one embodiment, the bottoms of the cavities have a diameter of 0 µm, which equals a sharp tip. In yet another embodiment, the bottoms of the cavities are flat with a diameter of 1 µm to 200 µm, which equals a frustrum. However, the most preferred embodiment consists of pyramidal cavities with spherical bottoms (rounded tips) in order to support cluster formation in a physiological way (FIG. 1D).

In case the cavity is a cone, the open diameter D of the cone is preferably from 10 µm to 5 mm, further preferred from 20 µm to 2.5 mm, more preferred from 100 µm to 1 mm and most preferred from 300 µm to 800 µm and the bottom diameter $d_1$ is preferably between 0 and 500 µm, more preferred from 1 µm to 350 µm, further preferred from 50 µm to 150 µm and most preferred from 75 µm to 100 µm. Without wishing to be bound by theory, the results from the experimental work with cell cluster size and cluster oxygenation demonstrate that a cluster diameter of 80 µm to 100 µm results in sufficient cluster core oxygenation as well as cluster functionality.

In case the cavity is a quadrangular pyramid with a rounded tip, the open diameter is being formed by four edges (c in FIG. 1C) which have a length ranging from preferably 10 µm to 5 mm, more preferred from 200 µm to 800 µm, further preferred from 400 µm to 585 µm and most preferred from 535 µm to 555 µm. The rounded tip has preferably a diameter $d_2$ between 0 and 500 µm, more preferred from 1 µm to 350 µm, further preferred from 50 µm to 150 µm and most preferred from 75 µm to 100 µm (Detail R, FIG. IE). In case the cavity is a pyramid with a frustrum, the pyramid has preferably a frustrum bottom area A of from 1 to 250,000 µm², further preferred of from 5 to 100,000 µm², more preferred of from 15 to 50,000 µm² and most preferred of from 1,000 to 15,000 µm². It is a further preferred embodiment of the device of the present invention when the cavity is in a pyramidal shape, wherein the pyramid has rounded edges.

It is a further preferred embodiment of the device of the present invention when the cavity is a quadrangular or trilateral pyramid.

Figure 1D:
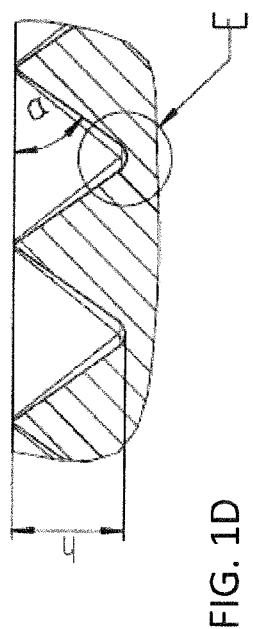

It is a further preferred embodiment of the device of the present invention when the rounded tip of the cavity has a radius r between 0 and 250 µm, preferably from 5 to 200 µm, further preferred from 20 to 100 µm and most preferred from 35 to 60 µm (Detail R, FIG. 1E).

It is a further preferred embodiment of the device of the present invention when the height h of the cavity is from 10 µm to 2000 µm, preferably from 50 µm to 1000 µm, further preferred from 100 µm to 500 µm and most preferred from 200 to 400 µm (h, FIG. ID). It is a further preferred embodiment of the device of the present invention when the top opening edge length c of the pyramidal cavity is from 10 µm to 5 mm, more preferred from 200 µm to 800 µm, further preferred from 400 µm to 585 µm and most preferred from 535 µm to 555 µm. In this context it is particularly preferred that the pyramid is a quadrangular pyramid.

Figure 1C:
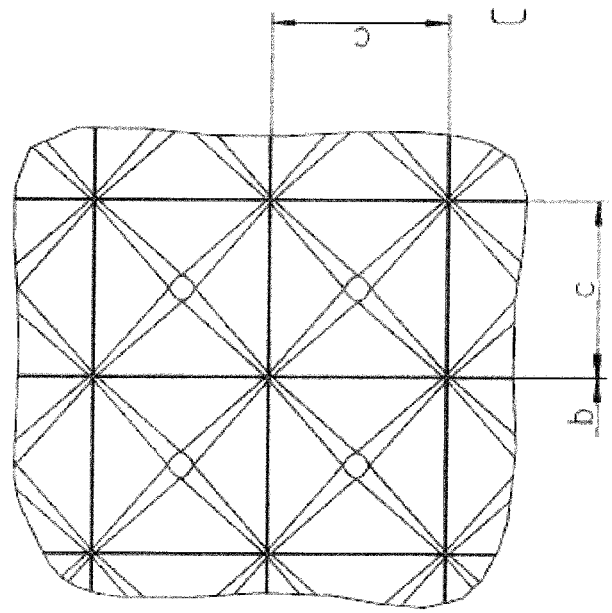

In a preferred embodiment of the present invention, the bottom of the device comprises from 1 to 1,000,000 cavities, preferably from 100 to 100,000 cavities, more preferred from 1,000 to 50,000 cavities and most preferred from 10,000 to 20,000 cavities. The cavities of the present invention are designed to be very close to each other: particularly, the top edges between the cavities are less than 15 µm broad in order to increase the number of aggregated clusters per surface (FIG. 1C). In a preferred embodiment of the present invention, the space between the cavities is therefore less than 30 µm, more preferred less than 20 µm, further preferred less than 18 µm and most preferred less than 15 µm. This design with narrow top edges additionally helps to avoid cell loss or uncontrolled cytokine release of dying cells by avoiding cells to rest on the edges, so that every single cell slides down to the bottom of the cavities.

A further feature of the present invention is the use of defined wall angles. It is therefore a further preferred embodiment of the device of the present invention when the wall angle α of the cavity is from 35° to 75°, preferably from 40° to 70°, further preferred from 50° to 60° and most preferred 54.7° (α, FIG. 1D).

The shape, dimensions of the tissue culture well and tray containing the described cavities can vary depending on the needs of the user. For example, the tissue culture well can be circular, rectangular and the like. The size of the tissue culture well can be the size of a typical 384 well (compartment) plate, a typical 96 well tissue culture plate, a typical 24 well tissue culture plate, a 12 well tissue culture plate, a 6 well tissue culture plate and the like. The system can also be in the shape of a tissue culture flask. Additionally, the defined ground cavities can be introduced into other carriers such as cell culture plate inserts.

Figure 2C:
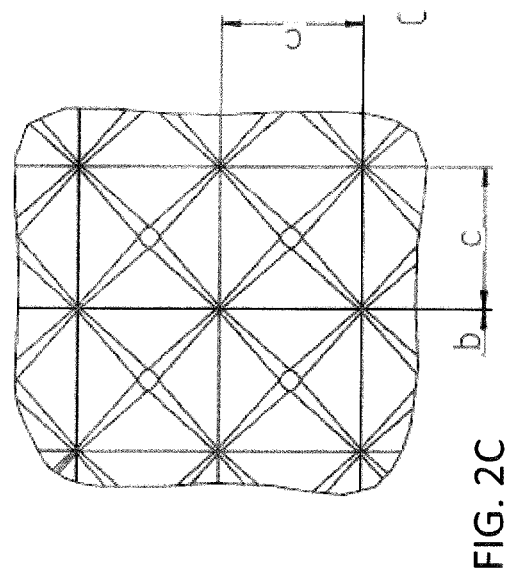
Figure 2D:
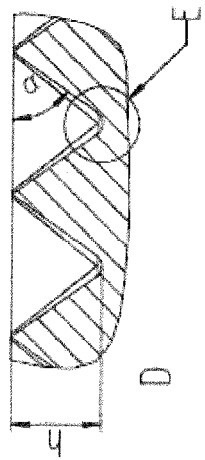
Figure 2E:
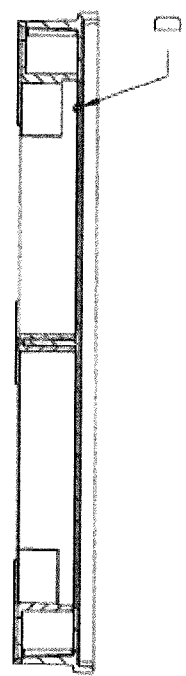
Figure 2E:
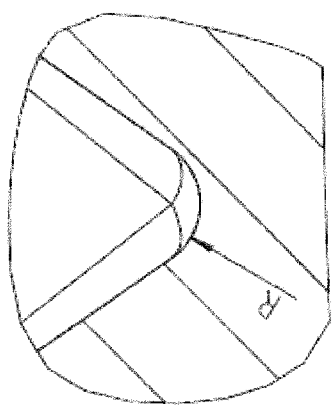
Figure 2G:
Figure 2P:
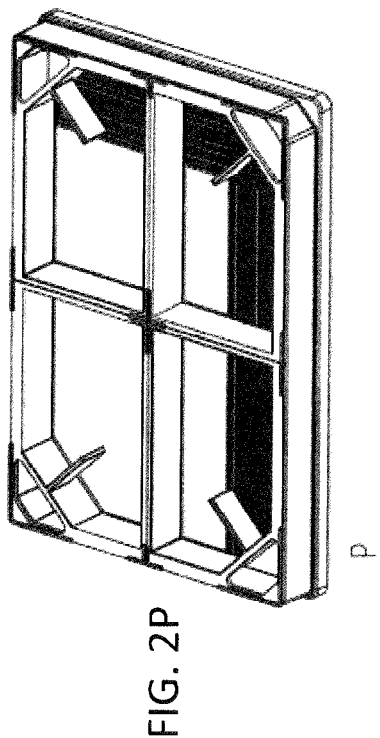
Figure 2H:
Figure 2H:
Figure 2J:
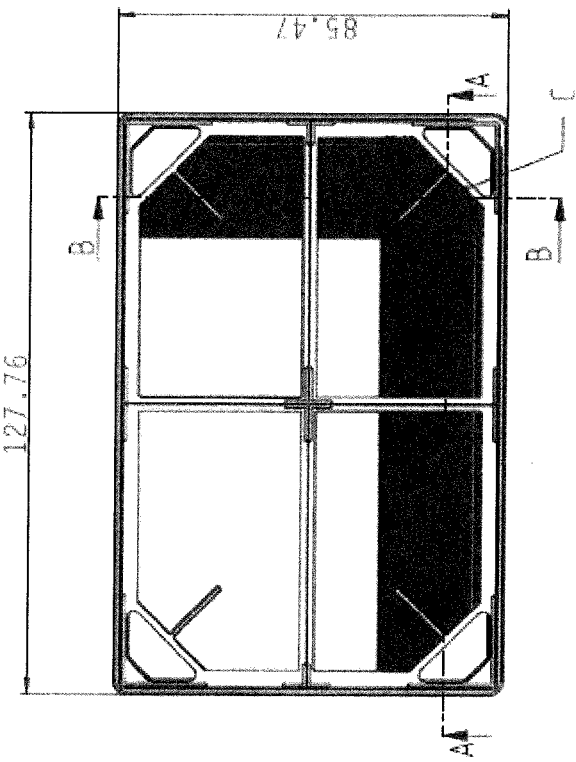
Figure 4P:
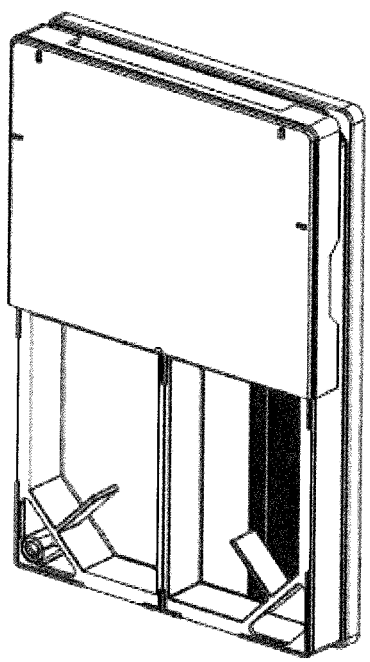
Figure 4G:
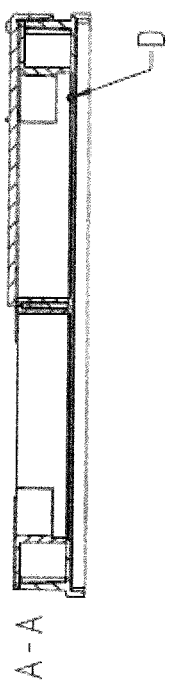
Figure 4G:
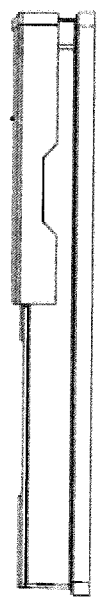
Figure 5D:
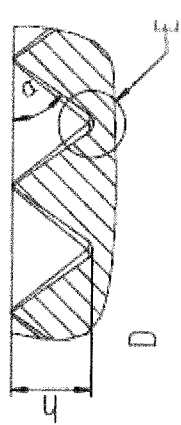
Figure 5C:
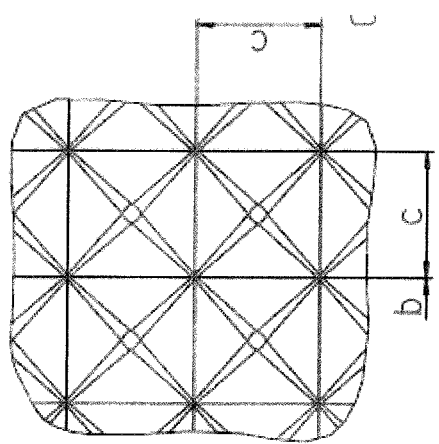
Figure 5G:
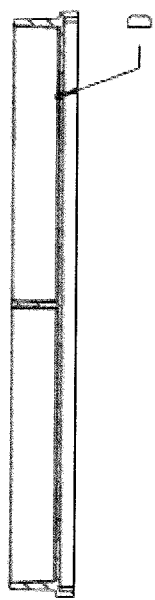
Figure 5G:
Figure 5E:
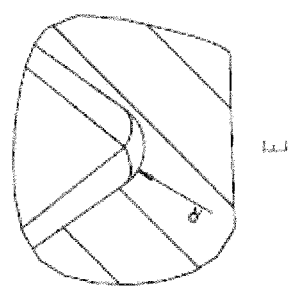
Figure 5P:
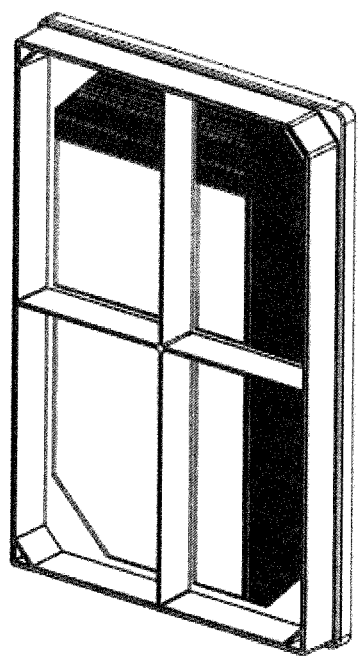
Figure 5H:
Figure 5H:
Figure 5J:
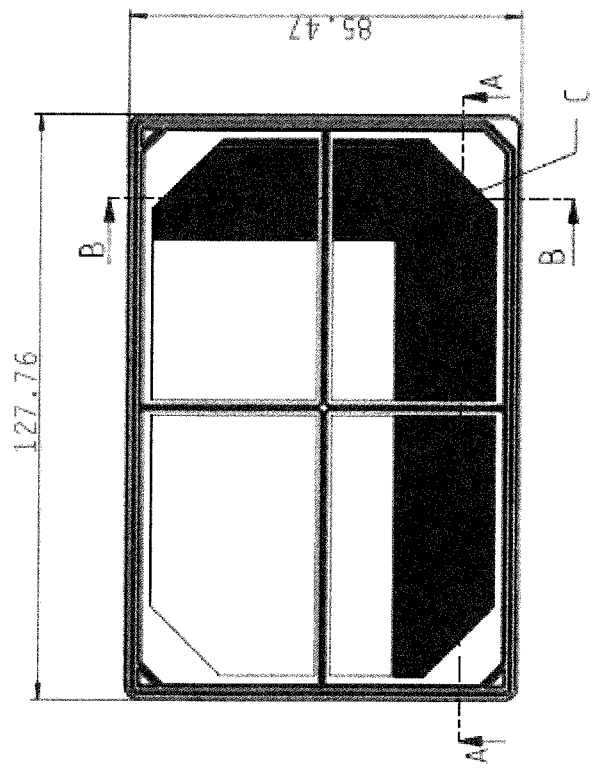
Figure 6:
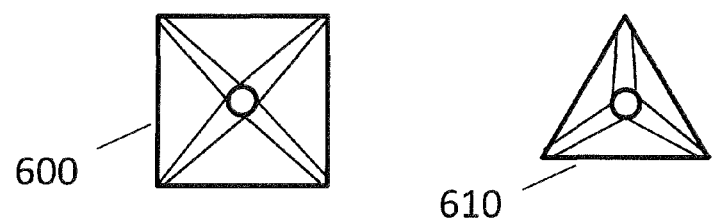
FIG. 6 shows a top-down view of a cavity 600 which is formed as a quadrangular pyramid and a cavity 610 which is formed as a trilateral pyramid.
Figure 7:
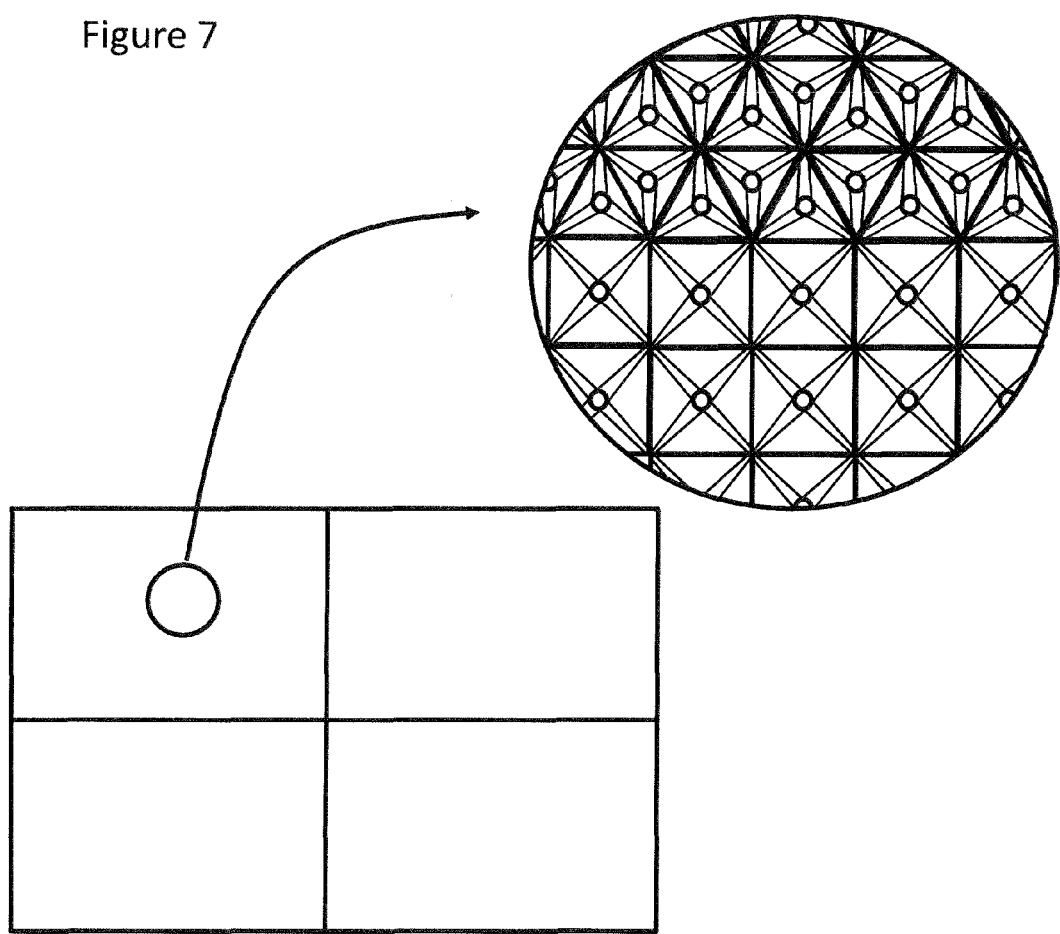
FIG. 7 shows a region of a compartment of cavities having different shapes and sizes, which is formed of an array of quadrangular pyramids 600 and trilateral pyramids 610 as depicted in FIG. 6.

The most preferred embodiment of the present invention is a SBS footprint standard cell culture plate (the same size of classical 6, 12, 24 or 96-well (compartment) plates, 127.76 mm long, 85.47 mm broad and 14-15.5 mm high, depending on whether filling inserts are in place or not) made of cyclic olefin copolymers (COC) or polypropylene or polystyrene in which the bottom of the plate is covered with the ground cavities as defined in FIGS. 2C, 2D, and 2E. The plate is equipped with a standard plate lid (FIG. 4P) assuring stable microenvironment and controlled gas exchange. The plate can be separated into different compartments/wells in order to provide more experimental or clinical possibilities of various cavity numbers per compartment. It is thereby particularly preferred that the plate comprises at least one compartment. In the case of one compartment, the plate per se constitutes the compartment. In the case of several compartments, the compartment may comprise the same or a different number of cavities, whereas the cavities of each compartment may be of the same or of different shapes and sizes. The latter feature also applies in the case of one single compartment. Further, the compartments may comprise cavities of the same or different shapes and sizes.

In this most preferred embodiment, the SBS footprint standard cell culture plate is either just one plate with the bottom comprising the pyramidal cavities with rounded tips or the cell culture plate is divided into different compartments/wells with the bottom of the compartments comprising the described cavities. The number of compartments/wells per SBS footprint standard cell culture plate can range from 1 to 384 per plate, more preferred from 1 to 96 compartments and most preferred from 1 to 24 compartments. The number of cavities per compartment is dependent on the respective compartment and cavity size and reaches 10,000 to 20,000 cavities if there is only one compartment, 5,000 to 10,000 cavities per compartment if there are two compartments and so on.

Figure 3P:
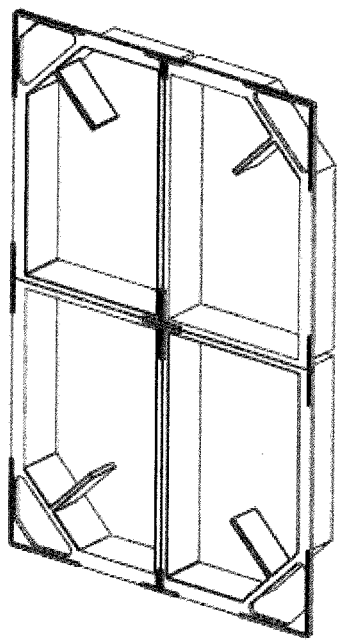
Figure 3P:
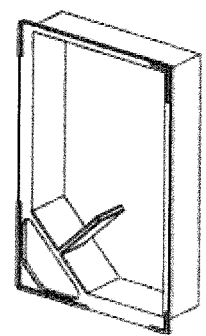
Figure 3G:
Figure 3G:

For illustrative purposes, the presented figures show the most preferred embodiment with four compartments of which the bottoms contain the described cavities. For technical reasons, between the walls of the compartments and the beginning of the cavities on the bottom, small borders are remaining, where single cells could rest after seeding instead of accumulating within the cavities. This should be avoided for experimental uniformity (i.e. avoidance of uncontrolled cytokine release, etc.). For that reason, in the most preferred embodiment every compartment of the present invention contains optionally at least one filling insert allowing the descent of every single cell to the ground cavities (FIGS. 2C, 2D, and 2E). This is made possible by the design of the inserts (FIGS. 3A-A, 3B-B, 3G, 3H, 3J and 3P, the preferable size of the inserts is shown in FIG. 3J with numbers given in millimeters; one insert is 62.05 mm long, 40.9 mm broad and 11.5 mm high with additional 0.5 mm small bridges for controlled gas exchange, either realized here (shown) and on the plate (not shown) or on the lid itself (not shown)). The inserts are preferably constructed in a way that the vertical walls of the inserts begin directly after the last cavities on the edges of the bottom end. This means that with the initial seeding of the single cell solution, every cell in this solution will descend to a ground cavity together with other cells and will form cell clusters. Cell "loss" of single cells not finding a ground cavity is therefore avoided. After this initial step, the filling inserts can be taken out for a later controlled medium change as described below. The inserts can be taken out of the compartments with the aid of a little handhold.

In a further preferred embodiment, every compartment contains in at least one edge at least one surface without ground cavities. This surface is preferably separated from the region with cavities by the walls of the filling inserts. After removal of the inserts, this surface allows the positioning of classical pipette tips of various sizes without harming the cavities and makes highly controlled medium changes possible (FIG. 5). The medium change is done by placing the pipette tip on this surface and slowly sucking the old medium away, which will be reduced by this construction to almost the level of the top edges of the ground cavities. The filling of the medium works the other way round by placing the pipette again on this surface and slowly letting the medium flow back. Three goals are reached by this construction: first, the medium is sucked away to a high degree, only little medium volume is remaining in the cavities themselves. Second, the medium change is performed in a uniform manner because sucking away the medium always results in the same remaining medium due to this construction. Third, the cells on the cavity grounds are not disturbed and/or flushed away during the medium change as it could happen when the medium change would be done by placing the pipette tip directly over the cavities.

In a further preferred embodiment, a further refinement of the medium change is possible by modifying the filling inserts in a way that they are placed back into the compartments for performing a medium change. This requires a design modification on the outside of the inserts, namely the introduction of small channels on the outside of the insert walls with various small openings on the bottom of the insert walls. Those of skill in the art will understand that by sucking the medium out from (or filling medium into) the space between the insert and the compartment (with the filling inserts placed within the compartments), the small channels will lead the medium from and to the ground cavities through the small openings on the bottom of the insert walls from all four borders and not only unilaterally as it is shown here in the most preferred embodiment (where the medium change is done without the inserts in place).

With these structures and a realization in a SBS footprint standard cell culture plate it is possible to reach a cluster number of roughly 10,000 to 50,000 per plate, depending on the cavity size.

The present invention further pertains to a method for aggregating cells, comprising:
a) providing a device comprising at least one cavity for receiving one or more than one cell, wherein the cavity is in a conical shape or pyramidal shape;
b) seeding from 0 to 100,000 cells per cavity;
c) letting cells aggregate within the cavities by gravity or centrifugation;
d) before the first medium change, taking out of the filling inserts;
e) performing the medium change in a controlled manner by placing the pipet tip on a filling surface, where an old medium is being sucked away and a new medium is being pipetted in without disturbing the cells in the cavities;
f) cultivating and experimenting with cell clusters, medium composition, oxygen tension and further parameters according to the experimental needs;
g) harvesting aggregated cell clusters by soft medium jet with a pipet or by negative centrifugation;
h) utilizing the aggregated cell clusters according to experimental or clinical needs.

Those of skill in the art will understand that the production method of the present invention can consist of (but is not limited to) various technologies such as corrodation, SU 8, high-speed cutting, Laser glass structuration or direct steel structuring. In a preferred embodiment, the present invention is designed by the use of a tool insert which was created based on a microstructured master through galvanic separation. The bottoms of the cavities are made spherical by the use of further chemical and/or mechanical refinement steps. In the most preferred embodiment, a silicon master is corroded, from this master a nickelshim is galvanically separated and this nickelshim is electropolished (which produces the spherical bottoms). The nickelshim(s) are then inserted into a tool for the casting of the SBS footprint cell culture plates.

In yet another embodiment, the tissue culture well with the defined ground cavities is made from at least one material comprising polypropylene, polystyrene, vinyl, other plastics, metals, alloys, minerals, non metallic minerals, wood, fibers, cloth and glass. The tray comprising at least one or more tissue culture wells is made from at least one material comprising polypropylene, polystyrene, vinyl, other plastics, metals, alloys, minerals, non metallic minerals, wood, fibers, cloth and glass.

Finally, the present invention pertains to the use of a device as defined before for the aggregation of cells.

It is understood that the foregoing description is that of the preferred embodiments of the invention and that various changes and modifications may be made thereto without departing from the spirit and scope of the invention as defined in the appended claims.

What is claimed is:
1. Device for the aggregation of cells,
wherein the device comprises a plurality of cavities for receiving one or more than one cell,
wherein the cavities are pyramidal cavities having spherical bottoms with rounded tips,
wherein the pyramidal cavities have rounded edges between the rounded tips and respective bases of the pyramidal cavities,
wherein a space between the cavities is less than 20 µm, and
wherein a radius of the rounded edges increases from a first radius at the bases of the pyramidal cavities to a larger second radius at the rounded tips.
2. Device according to claim 1, wherein the pyramidal cavities are quadrangular pyramids.

3. Device according to claim 1, wherein a radius r of the rounded tips is between 0 and 250 μm.

4. Device according to claim 1, wherein a height h of the cavities is from 10 μm to 2,000 μm.

5. Device according to claim 1, wherein a wall angle α of the cavities is from 35° to 75°.

6. Device according to claim 1, wherein an edge length c of the cavities is from 50 μm to 2000 μm.

7. Device according to claim 1, wherein the device comprises from 2 to 1,000,000 cavities.

8. Device according to claim 7, wherein the device comprises from 10,000 to 20,000 cavities.

9. Device according to claim 1, wherein the device further comprises at least one compartment of cavities, the cavities having the same or different shapes and sizes.

10. Device according to claim 9, wherein the at least one compartment also comprises filling inserts.

11. Device according to claim 10, wherein the at least one compartment comprises at least one surface without cavities.

12. Device according to claim 11, wherein the at least one surface is located on at least one edge of the at least one compartment.

13. Method for aggregating cells, comprising:
a) providing a device as defined in claim 1;
b) seeding from 0 to 100,000 cells per cavity;
c) aggregating cells within the cavities by gravity or centrifugation;
d) before a first medium change, taking out of filling inserts;
e) performing a first medium change in a controlled manner by placing a pipet tip on a filling surface, where an old medium is being sucked away and a new medium is being pipetted in without disturbing the cells in the cavities;
f) cultivating and experimenting with cell clusters, medium composition, oxygen tension and further parameters according to the experimental needs;
g) harvesting aggregated cell clusters by soft medium jet with a pipet or by negative centrifugation; and,
h) utilizing the aggregated cell clusters according to experimental or clinical needs.

14. Method of generating uniform cell clusters, comprising aggregating cells in a device as defined in claim 1.

* * * * *